United States Patent [19]

O'Neal et al.

[11] Patent Number: 5,368,042

[45] Date of Patent: Nov. 29, 1994

[54] BIOFEEDBACK DEVICE FOR MONITORING MUSCULAR MOVEMENT

[76] Inventors: John L. O'Neal, 1002 Nightingale Blvd., Stillwater, Minn. 55082; Peter J. Vogelgesang, 3033 N. Albert St., Roseville, Minn. 55113

[21] Appl. No.: 762,918

[22] Filed: Sep. 19, 1991

Related U.S. Application Data

[63] Continuation-in-part of Ser. No. 364,621, Jun. 9, 1989, abandoned.

[51] Int. Cl.$^5$ ............................................. A61B 5/04
[52] U.S. Cl. ................................. 128/733; 128/905; 128/782; 273/183.1; 273/186.1
[58] Field of Search ............... 128/733, 644, 903, 905, 128/782; 273/183 B, 186 R, 188 R, 189 R

[56] References Cited

PUBLICATIONS

*Electronyographic Sensor Design for Use with an Externally Powered Prosthetic Arm,* by Robert L. Konigsberg, Proceedings of the 23rd IEEE Annual Conference on Engineering in Medicine and Biology, Nov. 30, 1970, p. 240.

*An engineering contribution to the appraisal of intra-stroke canoeing technique,* by J. R. Court, J. K. Davis and J. Atha, Engineering in Medicine, vol. 9, No. 3, Jul. 1980, pp. 130–136.

*Electromyographic Analysis of the shoulder during the golf swing,* by Marylin Pink, MS, PT, Frank W. Jobe, M.D., and Jacquelin Perry, M.D., The American Journal of Sports Medicine, vol. 18, No. 9, 1990, pp. 137–140.

*Loosen Up and Turn on the Power,* by Tom Paxson, Feb. 1990/Golf Digest, pp. 69–73.

*Get a Grip on It!,* American Golf Magazine, Jun./191 pp. 42–44.

*Weight Shift* by Lew Fishman, Apr. 1989/Golf Digest, pp. 133–141.

*Rotator cuff function during a golf swing\** by Frank W. Jobe, M.D., Diane R. Moynes, MS, RPT, and Daniel J. Antonelli, PhD, The American Journal of Sports Medicine, vol. 14, No. 5, 1986; pp. 388–392.

*Electromyographic shoulder activity in men and women professional golfers* by Frank W. Jobe, M.D. Jacquelin Perry, M.D. and Marilyn Pink, MS, PT, The American Journal of Sports Medicine, vol. 17, No. 6, 1989, pp. 782–787.

*Primary Examiner*—Kyle L. Howell
*Assistant Examiner*—John P. Lacyk
*Attorney, Agent, or Firm*—John C. Barnes

[57] ABSTRACT

A swinging movement in an impact sport activity, such as golf, tennis, baseball or the like, can be monitored to analyze the skill of the player by a biofeedback mechanism which measures electrical impulses created by activated nerves as muscles tense. The mechanism includes a band adapted to be placed about an arm and/or leg of the player, the band includes a pair of electrodes adapted to contact the muscle, differential amplifier means accepting the electrical voltage from the muscle, means for measuring the amplified voltage, and reporting means affording an indication of the results of the swing, such recorder including a sound emitting device, or a transmitter and computer, recording device, or printer. Preferably, the mechanism also includes a device for signalling the point of impact with an object.

18 Claims, 9 Drawing Sheets

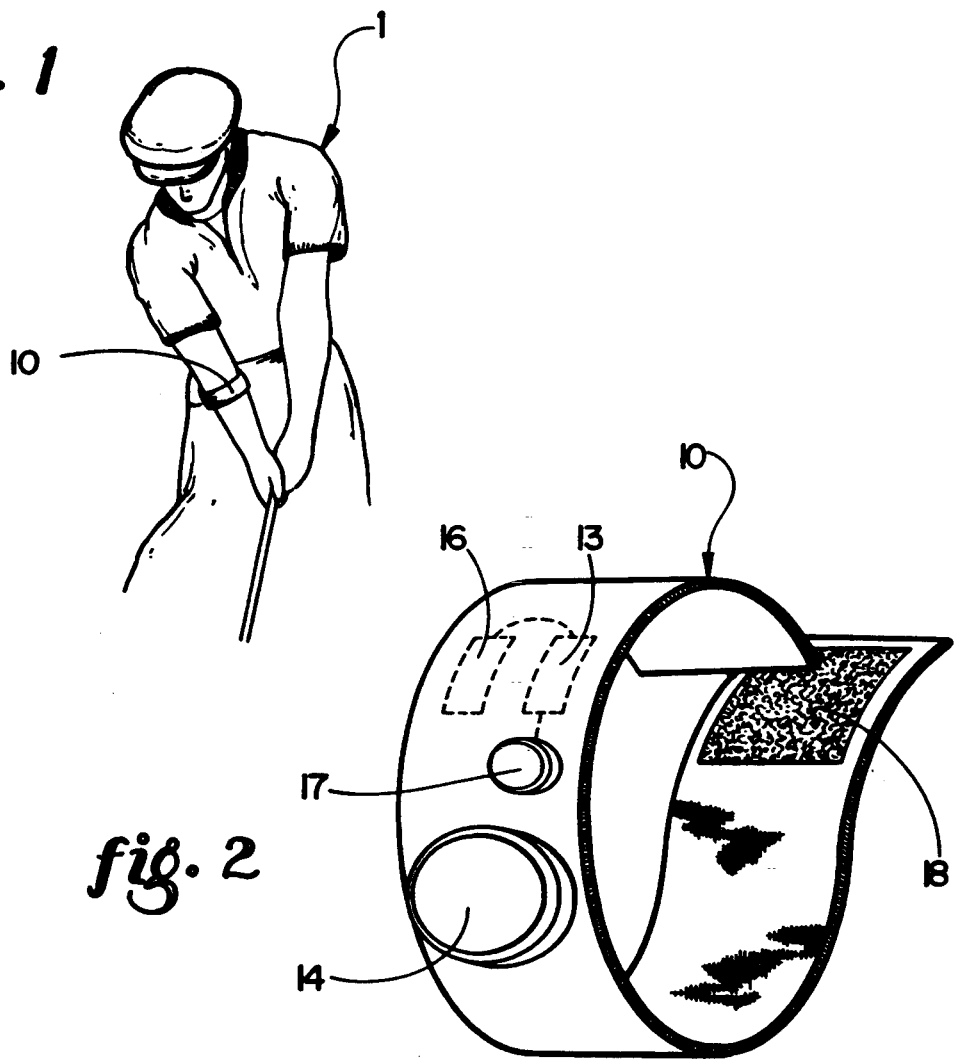
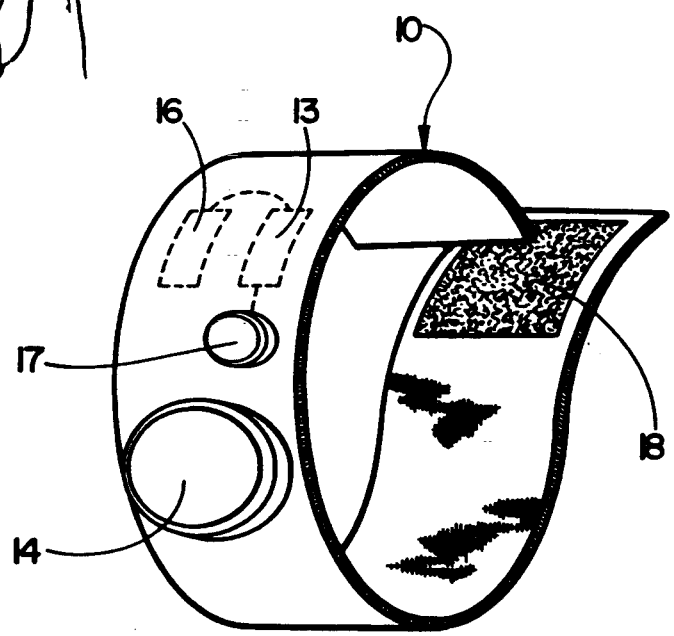
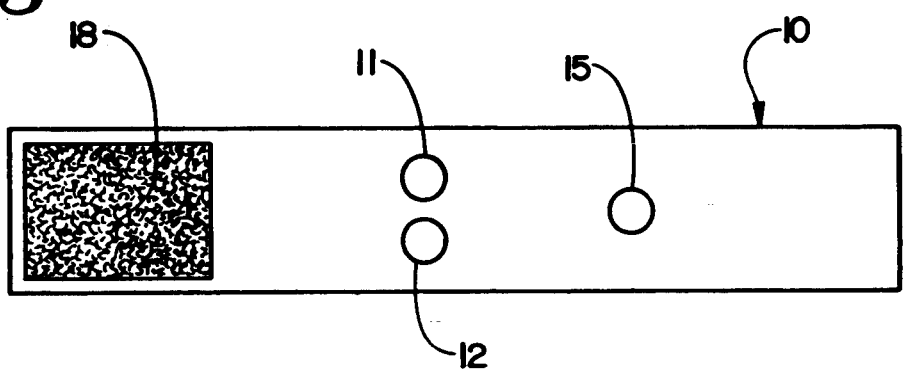

BIOFEEDBACK DEVICE FOR MONITORING MUSCULAR MOVEMENT

This application is a continuation-in-part of application Ser. No. 07/364,621, filed Jun. 9, 1989, now abandoned.

FIELD OF THE INVENTION

The present invention relates to sports methods and equipment. More particularly the present invention relates to biofeedback devices used in developing sports skills.

BACKGROUND OF THE INVENTION

A wide variety of devices have been developed in the past for use in teaching sports skills. In some instances, the devices have included mechanism for limiting body movement. For example, U.S. Pat. No. 3,608,896 shows a device for restraining leg movement in teaching figure ice skating. In other instances, the devices have included strain gauges that determine the force exerted by a particular muscle. One such device is marketed by Integrated Sports Electronics, Inc. under the mark StrokeMaker.

There has been a long standing need for methods and devices for use in teaching sporting skills wherein the device does not interfere with the body movement. Any interference, of course affects the body movement, and thus has limiting effects when used in teaching sporting skills. If a strain gauge is used in teaching tennis, the device itself may change the arm movement of the tennis player. Likewise, a muscular restraint in golf makes the swing unnatural and results in a different feel than is encountered when the device is not present.

Strain gauges are illustrated in U.S. Pat. No. 4,501,148 (Nicholas et. al.). In this instance, the strain gauge is used primarily to measure muscle force. Another such device is illustrated in U.S. Pat. No. 4,103,896 (LaRang). This device provides a gripping mechanism on a golf club to signal excess force when gripping by the off target hand. In another instance, an accelorama curve is provided for measuring acceleration or velocity in the swing, for example, of a bat or golf club. This device is shown in U.S. Pat. No. 3,717,857 (Evans). In each instance, the device adds significantly to the weight and feel of the bat or golf club, and thus produces an unnatural swing feel. The present invention provides a device free of such inherent disadvantages.

SUMMARY OF THE PRESENT INVENTION

The present invention provides a biofeedback mechanism which recognizes electrical impulses created by the nerves activating selected muscle groups. The sensing device may determine the timing of a muscle contraction by identifying when the electrical impulse is created. In other instances, the device may determine the magnitude of the electrical impulse and thus the magnitude of the muscle contraction.

The present invention includes mechanism for measuring electrical impulses created by activated nerves and mechanism for indicating the timing and magnitude of the electrical impulse. The mechanism for measuring the electrical impulse may include a light weight band carrying a plurality of electrodes. The weight may be equivalent to a wrist watch. The band may be simply a light weight elastic cloth sized to snugly, but not restrictively, surround the muscle involved, for example, the muscles of the forearm or the calf muscle of the leg. The electrodes may be mounted on the inner surface of the band, and may for example, be of metal foil or other conductive, low resistant material which may include polymers. In certain embodiments of the present invention, the band may include a radio transmitter. In other instances, the electrodes may be connected by a fine wire to a mechanism for measuring the magnitude of the electrical impulses, for example, a readout device such as a strip chart or a highly sensitive oscilloscope or computer. In those instances where a small radio transmitter is provided on the band, the readout device may include a radio receiver which reproduces the transmitted signal and feeds the signal to a strip chart recorder, oscilloscope or computer.

The method of the present invention includes measuring the electrical impulse of one or more muscle groups during an athletic skill movement, then comparing the magnitude of the electrical impulse at various points throughout the athletic skill movement to determine the muscle activation for example showing this muscle's coordination with other muscle activation as described in detail hereinafter.

IN THE DRAWINGS

FIG. 1 shows a golfer wearing a band of the present invention;

FIG. 2 is a perspective view of the band of the present invention;

FIG. 3 is a view of the inner surface of the band of the present invention;

Figure 8:
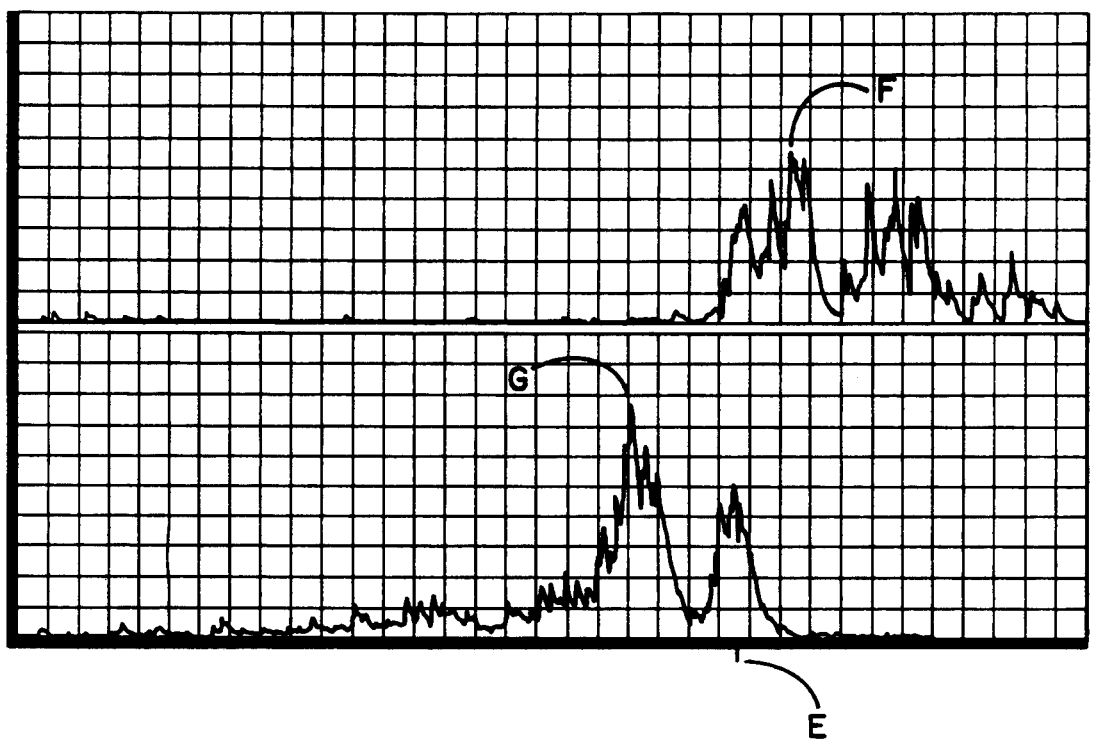
Figure 9:
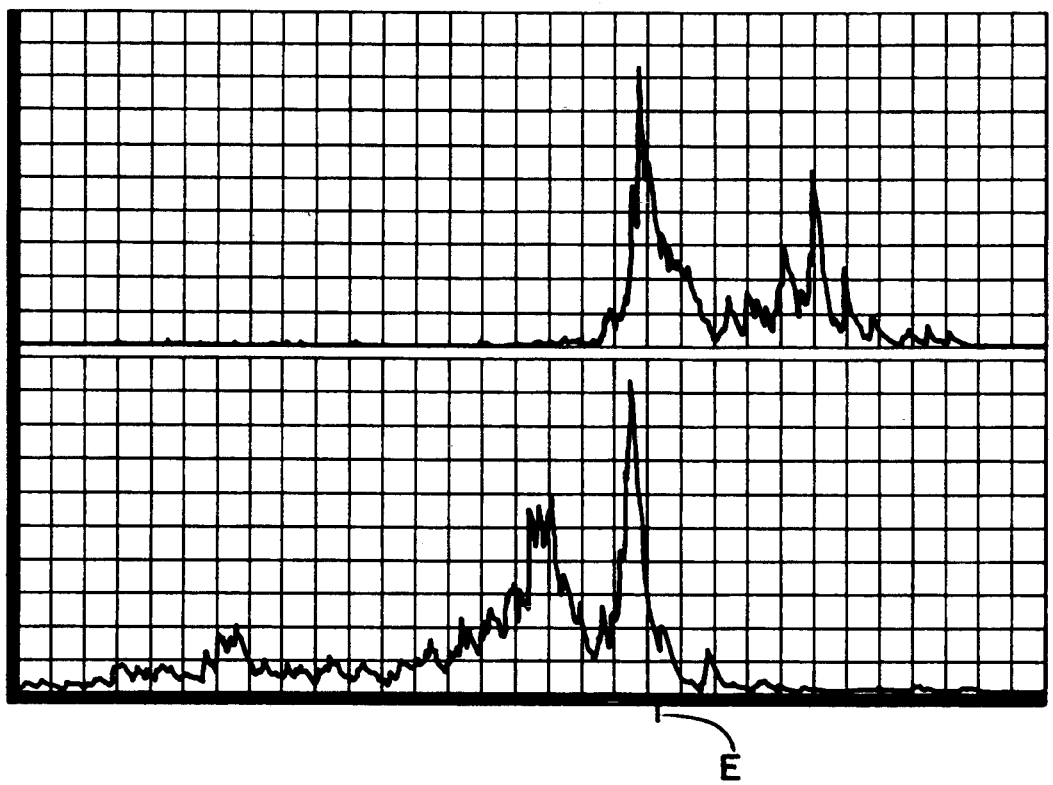
Figure 10:
Figure 11:
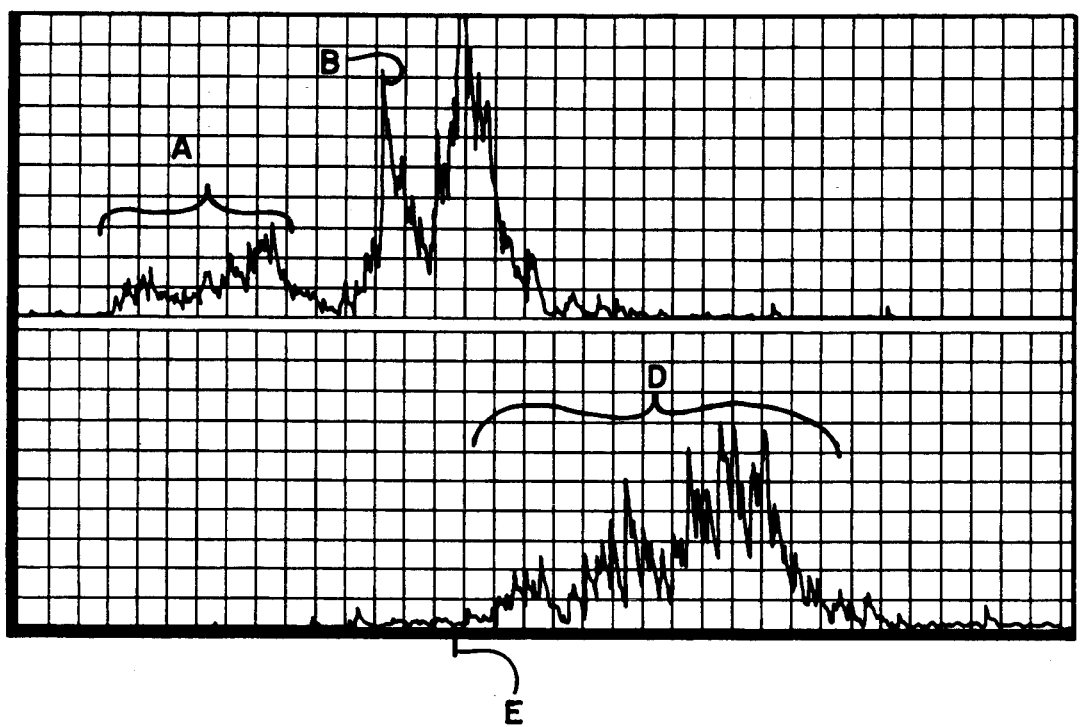
Figure 12:
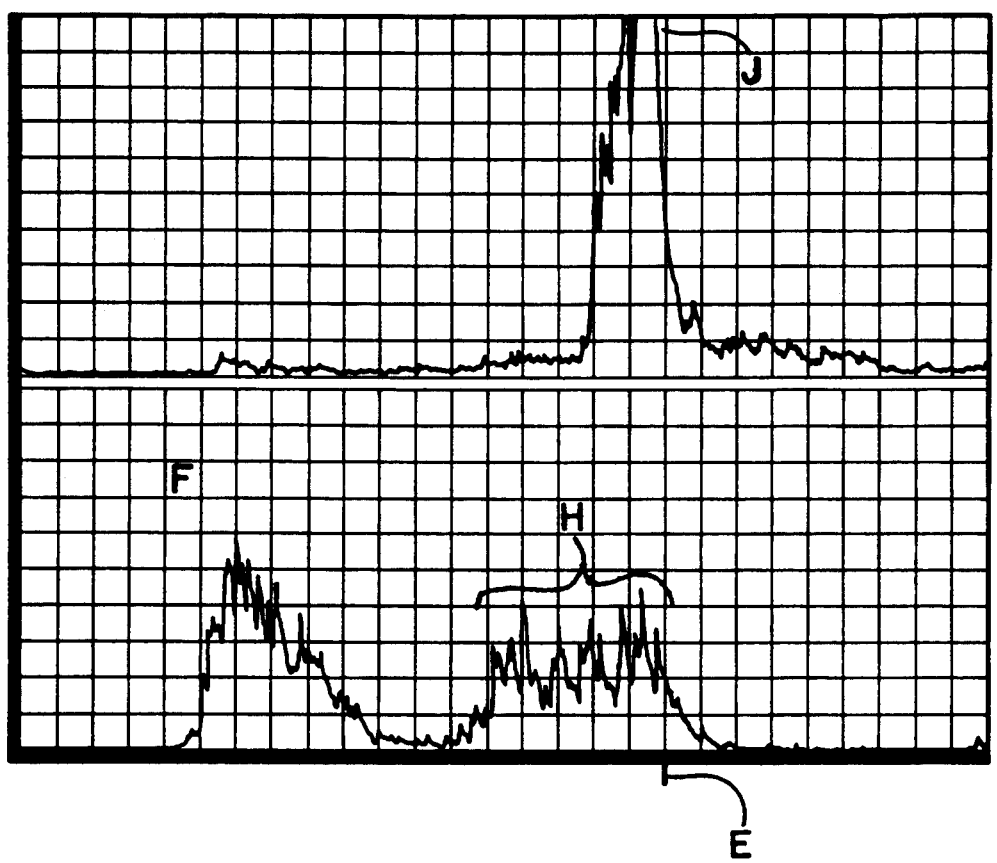
Figure 13:
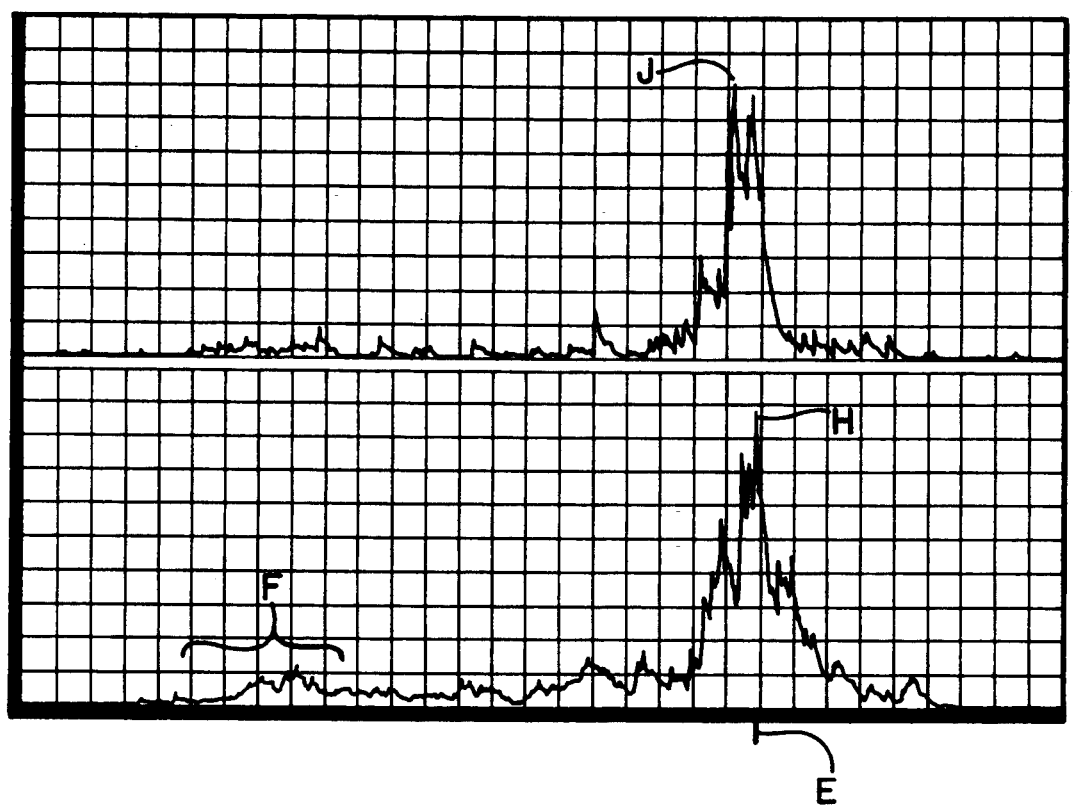

FIG. 8 is a graph of a left handed golfer with the upper portion of the graph showing the timing and magnitude of the electrical impulse from muscle producing the grip pressure of the leading hand of a golfer and showing in the lower portion of the graph the timing and magnitude of the electrical impulse from the muscle producing the grip pressure of the trailing hand of the golfer and is illustrative of a golfer having poor muscle movement coordination. The muscles for the two hands do not explode at the same time when impact with the ball occurs. The term "explode" and the like, as used herein, means a major and sudden muscle contraction;

FIG. 9 is a graph showing a pair of measurements during a golf swing of the golfer of FIG. 8 showing an improvement in the swing, this graph also showing in the upper portion of the graph the timing and magnitude of the electrical impulse from the muscle producing the grip pressure of the trailing hand of a golfer and showing in the lower portion of the graph the timing and magnitude of the electrical impulse from the muscle producing the grip pressure of the leading hand of the golfer;

FIG. 10 is a strip chart graph of a right handed golfer showing a pair of corresponding measurements during a golf swing, specifically the muscle producing the grip pressure of the leading hand in the lower portion of the graph and a leading calf muscle measurement in the upper portion of the graph;

FIG. 11 is a strip chart graph of a right handed golfer showing a pair of corresponding measurements during a golf swing, specifically the muscle producing the grip pressure of the leading hand in the upper portion of the graph and a leading calf muscle measurement in the lower portion of the graph. This chart depicts excessive grip during take-a-way from address point A, excessive grip pressure at top of back swing—point B and weight not transferred to left side until after impact with the ball—leading hand muscle explosion at impact with ball point C. This late movement to the left side, as shown in lower part of chart, is commonly referred to as a reverse pivot and is not desired of a consistent performer. The lower portion of the chart show an extended muscle contraction D well after impact of the club head with the ball rather than a desired explosive muscle contraction simultaneous with impact as shown in FIG. 10. FIG. 11 golfer is less skilled than golfer illustrated in FIG. 10;

FIG. 12 is a graph of a right handed hockey player showing in the lower portion of the graph the magnitude of the electrical impulse from the muscle producing the grip pressure of the leading hand of an amateur hockey player and showing in the upper portion of the graph the magnitude of the electrical impulse from the muscle producing the grip pressure of the trailing hand of the hockey player. This chart shows excessive grip with leading hand which will affect speed and accuracy of shot;

FIG. 13 is a graph of a right handed hockey player showing in the lower portion of the graph the magnitude of the electrical impulse from the muscle producing the grip pressure of the leading hand of a professional hockey player and showing in the upper portion of the graph the magnitude of the electrical impulse from the muscle producing the grip pressure of the trailing hand of the hockey player. This Figure shows the coordination and simultaneous muscle explosion in the left and right hands as compared to an amateur in FIG. 12. Muscle explosion for the professional hockey player, FIG. 13 is very similar to the professional golfer, FIG. 7 when the ball or puck is struck.

DETAILED DESCRIPTION OF THE INVENTION

A golfer 1 is illustrated in FIG. 1 using the arm band 10 of the present invention. The band 10 may be an elastic strip of fabric forming a band which is held by friction around the forearm of a golfer at a point just below the elbow. Mounted on the inside of the band are two electrodes 11 and 12 and a ground 15 as illustrated in FIG. 3. Mounted within the band is a battery operated electronic amplifier 13 and a visual/audible indicator 14. The band may have a replaceable battery 16 and an on/off compressible switch 17. In lieu of battery 16, a solar cell or cells may be used. The band 10 may include adjustable securing mechanism such as a VEL-CRO TM hook and loop fastener piece 18.

Muscle activity in the human body is initiated by electrical nerve impulses from the brain. These impulses may be measured at the surface of the skin by the voltage differential between electrodes 11 and 12. The magnitude of the electrical activity varies proportionally with the force the muscles are commanded to exert. Thus, when the differential signal from electrodes 11 and 12 is measured, the measurement indicates timing and magnitude of the force of the gripping action of the fingers of the hand. Preferably, the electrodes 11 and 12 are spaced, for example, 1 inch to 3 inches, and are aligned with the length of the forearm. The electrical voltage developed by the nerves is of course very weak. Therefore, a high gain electronic amplifier is used to magnify the amplitude of the electrical muscle signals. Desirably, a differential amplifier 13 which measures only the difference in voltage between the two electrodes is used, thus eliminating interfering electrical fields such as from power lines, static charges and the like. The amplified electrical signal may be of several volts.

The amplified signal is fed to an reporting or indicator device 14. The device 14 may be any suitable visual or audible device, analog meter, light emitting diode, or liquid crystal display. The device can be a bar graph liquid crystal display. Switch mechanism may be used to switch between visual and audible devices. The length of the darkened bar of the graph may be proportional to the force exerted by the fingers in gripping the golf club.

The device 14 may further or alternatively include an audible indicator which varies in pitch or a constant tone with variable intensity. Thus, the tighter the grip, the higher the pitch or louder the tone. Different tones may exist when multiple muscle groups are being monitored for coordination. Alternatively, the audible indicator may have an intermittent tone with the rate of sound pulses indicating the force of the grip on the golf club.

The device 14 may further or alternately include means for electrical shock or create a vibration for the student to recognize when improper muscle coordination occurs.

The electrodes 11 and 12 are desirably made of silver or a silver plated disc. Alternatively, nickel, tin, or stainless steel electrodes may be used. The electrodes desirably provide high conductivity and low resistance, and yet resist corrosion from perspiration and body chemicals.

Any suitable amplifier may be used. For example, the circuit illustrated in U.S. Pat. No. 4,170,225 (Criglar et al) is suitable. The amplifier may include mechanism for immediately reporting the signal. Alternatively, electronic design may include mechanism for storing the visual signal, thus permitting the golfer to swing, then activate the playback mechanism and observe the visual signal or display when a golf club contacts the ball, baseball bat contacts ball, etc., for other sports.

The storing device may be a video recorder, e.g., VCR. The VCR may record both the actual swing of the golf club and the graph showing the force exerted. The storing device may use a very high speed camera which then provides a recording that is particularly adapted to replay in slow motion. The recording can be of a known type that permits conversion to stick figures with colored representation of selected muscle.

Mechanism may be provided for detecting an event, e.g. a club head striking the golf ball. The device for sensing contact of the ball may be audio, optical or laser beam and serve as an event marker for point of reference. The device, for example, may further include an event marker such as mechanism that is sensitive to sound. The event marker places a mark on the visual signal or display. Any of various known devices for converting sound to an electrical signal may be used.

The graphing device then converts the electrical signal which is then converted into a mark on the graph. An illustrative sound sensing mechanism is sold by Digi-Key as Part No. 263C.

In various sports, the coordination of two or more muscle groups result in proper execution of the sports skill. For example, in a golf swing, the hands grip the club very lightly, until force is applied by the forearm muscles acting on the fingers of the hands when contact occurs with the ball. The forearm muscles are substantially relaxed except at the time point where the club contacts the ball. If the relaxed condition is not achieved, the golfer will lose control of the direction of the ball (e.g., resulting in a slice or hook) and the distance the ball travels will be reduced. If the levels or peaks in amplitude are observed, the golfer is notified that the muscle activation is improper and correction is explained.

Alternate Embodiment

Figure 4:
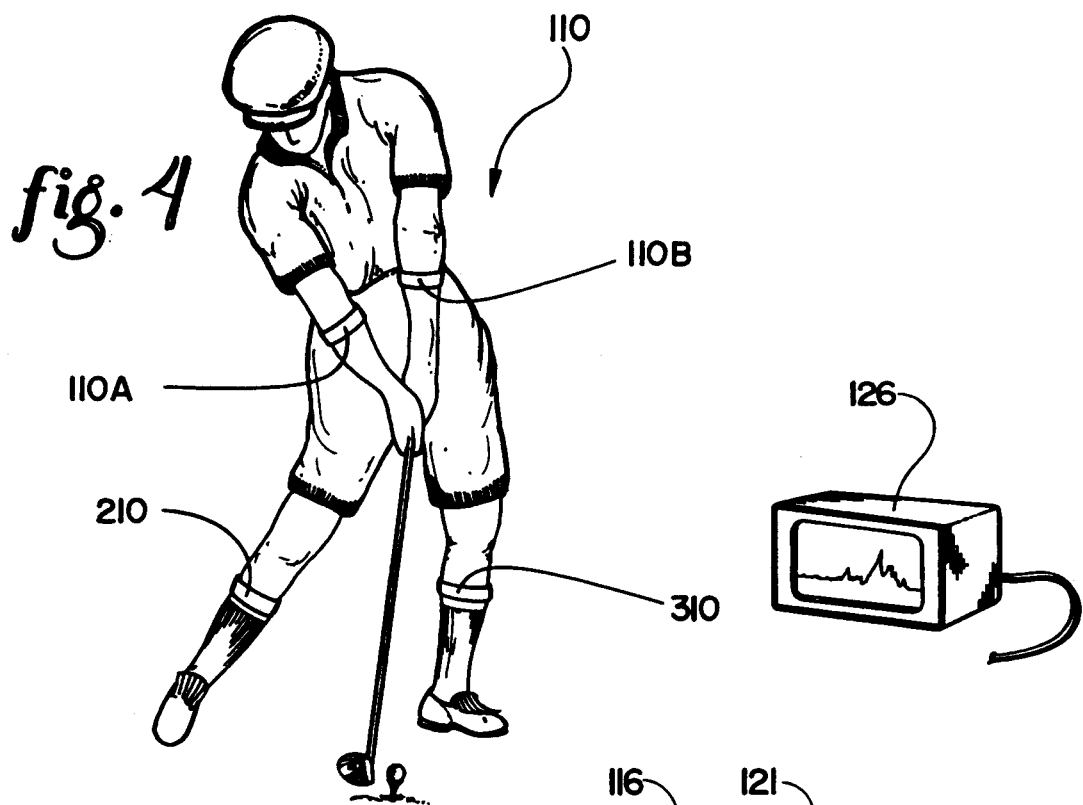
FIG. 4 through 6 are views of an alternate embodiment of the present invention.
Figure 5:
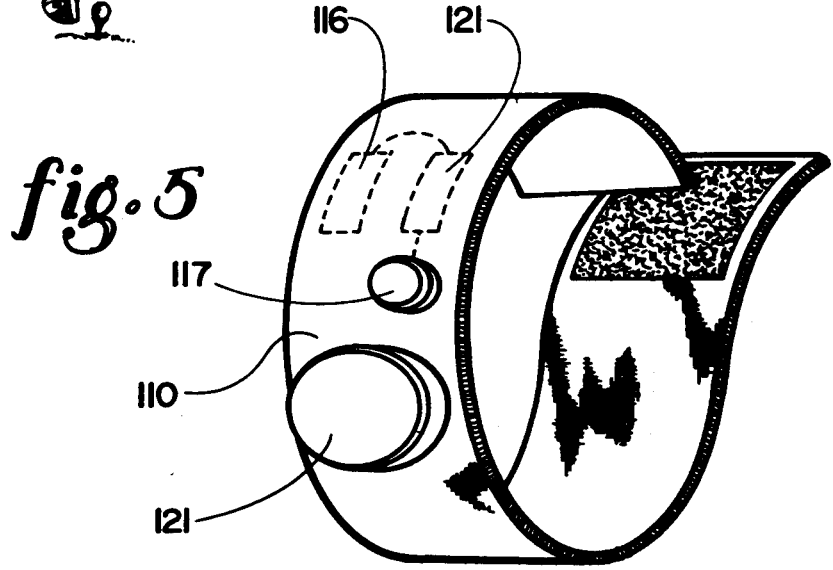
Figure 6:
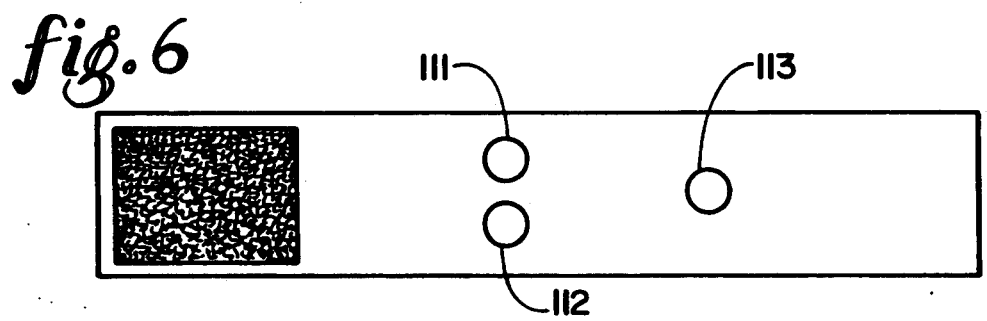

An alternate embodiment 110 of the present invention is illustrated in FIGS. 4 through 6. Training device 110 includes an elastic band similar to band 10; e.g., however, it further includes a small radio transmitter. The device 110 has a pair of electrodes 111 and 112 and a ground 113 which are connected to an amplified radio transmitter 121. The radio transmitter 121 may be powered and controlled in a manner very similar to the display 14 of device 10. In other words, the radio transmitter 121 may be powered by a battery 116 and activated and deactivated by switch 117.

A suitable receiver is provided in conjunction with a remote readout device such as a computer and display or strip chart 126. The strip chart or computer 126 prints a chart of the muscle activity during a sporting skill movement (e.g., a golf swing). The printed chart has several advantages. For example, it permits the accumulation of several golf swings, thus permitting comparison between different golfers or sequential swings of the same golfer.

The strip chart recorder or computer 126 includes a radio receiver which amplifies the signal and converts the signal into needle movement or activate a print head, thus graphing the chart. Alternatively, the radio receiver may drive an oscilloscope or computer and may electronically store the signal for later review and comparison. This embodiment may also include another band to measure the activity of a second muscle group. This may be the activity of the lead leg calf. Since readings are taken simultaneously, the activity of the leg muscles can be studied in association with the location of the golf club in the back swing, top of swing, impact, forward swing and follow-through. Software design could be used to simulate the position of the club throughout the swing or an actual video with spilt screen could show activity relative to a student's movement.

Figure 7:
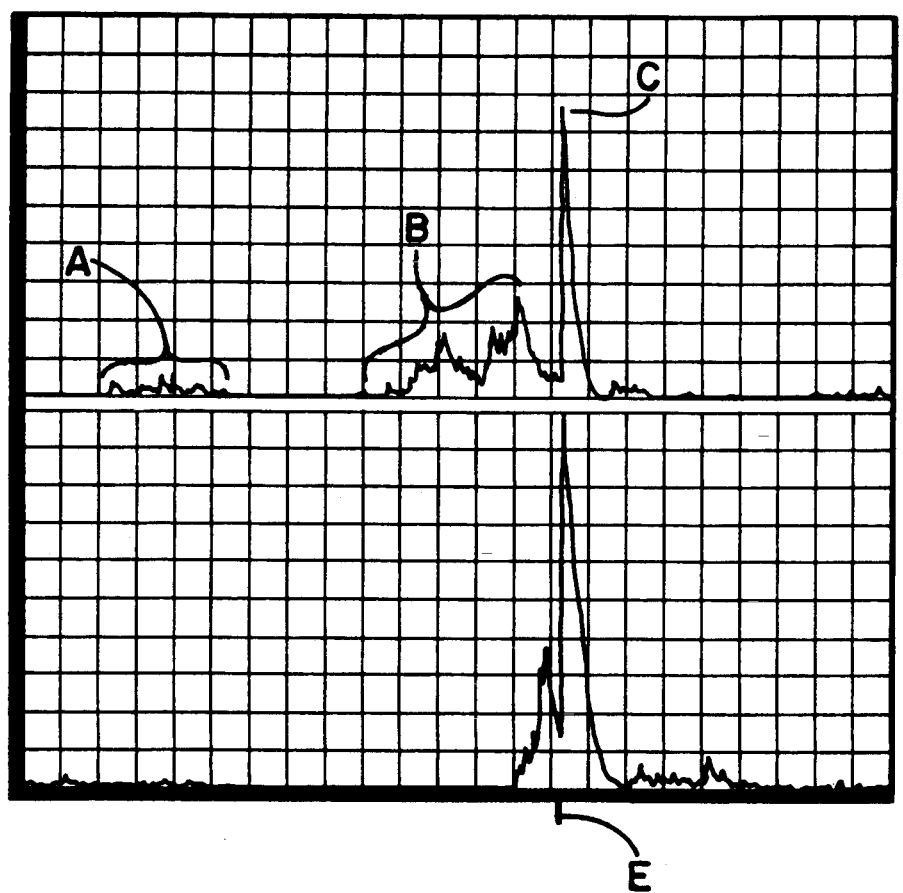
FIG. 7 is a graph of a right handed golfer with the lower portion of the graph showing the timing and magnitude of the electrical impulse from the muscle producing the grip pressure of the trailing hand of a golfer and showing in the upper portion of the graph the timing and magnitude of the electrical impulse from the muscle producing the grip pressure of the leading hand of the golfer.

Charts illustrated in FIGS. 7 and 8 show results of a good golf swing and a poorly executed golf swing, respectively. The good golf swing is shown in FIG. 7. Point A identifies the activity of the leading arm, namely, a slightly increased grip during address when the golf club is taken away from the golf ball and moves in an upward arc. Point B shows the muscle activity increasing after the top of the swing and just prior to impact with the ball, and Point C illustrates the muscle activity at the time the golf club impacts the ball.

Throughout the various graphs, Point E illustrates the point of impact of the club head with the ball. The impact may be sensed by a photo device e.g. recognizes that the ball is no longer present. The impact may be sensed by a sound sensing device that is activated by the click of the ball when struck by the club head. The impact device is coupled to the graph printer to create a mark E on the graph at the point when the ball is struck.

FIG. 8 shows graphing of muscle explosion occurring at two different distinctive times which illustrates poor coordination, e.g. points F and G.

A similar review of Figure XI shows a golf swing in which the club is strongly gripped throughout much of the swing. Repeating this swing in tournament play where body tension increases would be very difficult. Point A illustrates grip pressure at address and during backswing, Point B illustrates gripping the club at the top of the backswing and then a relaxation occurring prior to Point C (impact with ball). An improved swing would reflect no grip pressure at points A and B. To eliminate these points larger muscles in the back, shoulders, hips and legs must be used to move the golf club.

The graphs such as those illustrated in FIGS. 8 and 9 alert the golf instructor to problems in the golf swing of the student. These graphs represent muscle activity the instructor cannot observe without the use of the present invention. The instructor, using the present invention, can teach the student to change the golf swing, e.g. relax more prior to impact of the ball. The instructor may observe any of various other correctable defects in the student's swing by examining the graph produced during a golf swing by the student. For example over powering of one arm over the other may be observed.

FIG. 9 is a graph of the golfer of FIG. 8 following some instruction. It is to be noted that this golfer has now improved the coordination of the grip pressure of the left arm and right hand at the point of impact. Further it is to be noted that with these changes, the recorded magnitude of the muscle explosion at the point of impact is also substantially increased.

Timing of the muscle activation is illustrated in FIG. 10. The upper graph portion shows the muscle activity of the leading leg and the lower graph portion illustrates the muscle activity of the leading arm for a right handed golfer. Point B shows a strong muscle activation in the calf muscle at the point of impact E. Comparing the spikes C (left hand grip pressure) and B (left muscle) of the graph lines shows that the muscle activation of this golfer is well timed with both occurring simultaneously at the point of impact E. Point A is referred to as the forward kick (the first motion of transferring weight from the right to the left side).

Measurements of other muscle activity may be made during a sports skill movement, e.g., calf of trailing leg in golf swing, forearm of racket arm for tennis and the forearms and trailing arm in a hockey shot.

FIG. 12 is a graph of an attempted slap shot with a hockey stick showing the leading forearm and the trailing forearm muscle action of an amateur hockey player. Point F shows strong muscle activity in the leading forearm grip pressure during the take away action, i.e. moving the stick backward in preparation for the forward striking movement. The lower portion of the graph also shows muscle activation at the time of striking the puck with the leading hand. This muscle activation (Area H) is low in magnitude and spread over excessive time. This level of muscle activation (tension)

will decrease the ability to maximize hockey stick acceleration at impact with the puck. This same scenario would also apply to other athletic areas (golf, baseball and the like). The upper portion of the graph shows strong muscle activation (Point J) at the time of impact (Point E). In this example, maximum speed of puck and accuracy will not be witnessed as muscle activity is not coordinated as shown in FIG. 13 and hereafter described.

FIG. 13 illustrates a professional hockey player's muscle activity during a slap shot. It is to be noted that the muscle activity for leading and trailing forearms (grip pressure) is concentrated at the point of impact (Point E). The upper portion of the graph shows the muscle activity (grip pressure) of the trailing forearm and the lower portion of the graph shows the muscle activity (grip pressure) of the leading forearm.

While preferred embodiments have been illustrated in the FIGS. 1 through 6, various other modifications may be made without departing from the broader scope of the present invention. For example, in the case of golf, the signal may be carried by way of small electrical wires which extend upwardly along the upper arms and legs of the golfer 1 and then to the rear where they are connected to amplifiers and then the signal is sent to a strip chart device or computer similar to device 126.

The Method of the Present Invention

While the method of the present invention may be apparent from the descriptions of FIGS. 1 through 13, it will be further described hereinafter.

The method of the present invention includes a first step of measuring the electrical impulse emitted by the nerves activating the particular muscle or muscles involved. Next, the electrical signal is amplified and the amplified signal is used to communicate, for example, visually or audibly. The electrical signal at the surface of the arm, for example, may have a voltage of a few hundred microvolts. The amplification will typically increase the voltage to about 4 volts peak to peak. The latter range of voltage will be used to drive the liquid crystal device or other mechanism for display (e.g., the radio transmitter).

The preferred embodiment of the present method, a plurality of voltage measurements, are taken at various locations on the body. For example, the band 110A (Figure IV) may be placed on the right forearm of a right handed golfer and another bond 110B may be placed on the left forearm. Another band 310 may be placed on the left calf muscle, and a fourth band 210 may be mounted on the right calf muscle. Each of the bands 110A, 110B, 210 and 310 drive a separate needle on a strip chart or print head or are stored in a computer and printed via a computer printer or displayed on a computer monitor, all of which report the amplified differential voltage. For example, through radio transmitters operating at different frequencies, this provides for the creation of a strip chart or computer printout which illustrates coordination of these muscle groups in a timed or coordinated pattern. By identifying the point at which the ball is struck (Point E, FIG. 9), one can compare the muscle activity and coordination of that activity during a golf swing or for other athletic activities, (baseball, hockey, tennis and the like) with the point of impact.

While the arms and legs of the golfer have been used as the vehicle for describing the present invention, it is to be recognized that the apparatus and the method are equally applicable to various other muscle groups of the golfer and muscles used in other sports. The muscle groups may be leg, back or shoulder muscles. Other sports, for example, would include tennis, racket ball, baseball and the like. Other purposes in sports skills may be served by the device of the present invention, e.g., selection of club, bat, racket etc. The weight and size may be selected by consistency of optimum performance. The golfer shopping for new clubs may analyze his/her swing by the present invention to select the club weight and length that produces the most consistent and most desirable swing pattern on the graph.

While specific embodiments of the invention have been described, it is to be recognized that various modifications may be made without departing from the broader scope of the present invention.

What is claimed is:

1. A biofeedback device for monitoring muscular activity during a player's swing in an impact sport, said device including
  a band adapted for adjustment and securement around a muscle of a said player, said band carrying a pair of spaced electrodes adapted to contact the muscle for receipt of electrical voltage from the muscle surface, said electrodes being in continuity with differential amplifier means and means for measuring amplified differential voltage, and means for reporting the amplified differential voltage to indicate amounts of muscle tension over a continuum of a player's swing.

2. The biofeedback device of claim 1 wherein said means for reporting comprises an audible device and wherein the sound is emitted by said audible device when said muscle tenses.

3. The biofeedback device of claim 1 wherein said means for reporting comprises an audio feedback device.

4. The biofeedback device of claim 1 wherein said amplifier and said reporting device are contained in a wristwatch-sized package attached to the outside of said band.

5. A biofeedback device for use in monitoring the muscle activity during the swinging movement of a player in an ball impact sport, said device comprising
  a band adapted for securement around the arm of the player, said band carrying a pair of spaced electrodes adapted to contact the arm muscles for receipt of electrical voltage from the muscle surface during the swing movement, said electrodes being in continuity with differential amplifier means and means for measuring amplified differential voltage, means for reporting the amplified differential voltage to indicate muscle tension over a continuum of the swing, and means adapted for sensing the occurrence of impact when a player strikes a ball and for providing a signal.

6. The biofeedback device of claim 5 wherein said means for reporting the amplified differential voltage includes radio means for transmitting a signal representative of the amount of differential voltage received during the swing movement and means for remotely receiving said signal and converting said signal into a perceivable signal.

7. The biofeedback device of claim 6 wherein said means for converting comprises a strip chart recorder.

8. The biofeedback device of claim 6 wherein said means for converting comprises a computer and display to provide a chart.

9. The biofeedback device of claim 5 wherein said device includes battery means for powering said differential amplifier means.

10. A method for monitoring coordination of muscular activity of a player during a swinging movement during an impact sport activity to monitor the player's skill, said method comprising the steps of placing a pair of electrodes over a muscle to be monitored during the activity, continuously measuring the electrical field emitted by the nerves communicating with the muscle, amplifying the voltage to provide an electrical signal, reporting the magnitude of said electrical signal to a recording device, and sensing the point of impact during the swinging movement with an object and directing a signal to said recording device.

11. The method of claim 10 wherein said nerve electrical field is amplified to generate a signal and said method includes the step of transmitting the amplified signal to a remote reporting device.

12. The method of claim 11 wherein said transmitting step is by radio signal to a computer reporting device.

13. The method of claim 12 wherein said electrical field is measured at least at two spaced locations along a muscle.

14. The method of claim 12 wherein an electrical field is measured on each of two different muscles, one of said measurements serving as a bench mark for determining the timing of the movement of the second muscle.

15. A method for monitoring coordination of muscular activity during movement through a golf swing, said method comprising continuously measuring the electrical field emitted by the nerves communicating with a first muscle and reporting the magnitude of said first electrical signal as a reference point, wherein said first electrical signal is amplified, said amplified signal is transmitted to a remote location and the signal is converted at the remote location to perceivable signal, said transmission being by radio signal, continuously measuring the electrical field emitted by the nerves communicating with a second muscle and reporting the magnitude of said electrical signal to determine coordination of said second muscle with said first muscle, wherein said second measurement is amplified and transmitted to a remote location by radio signal, said radio signal being converted to a perceivable signal and reporting the first and second perceivable signals in conjunction with each other to display the degree of coordination of the two muscles.

16. The method of claim 15 wherein said activity is a golf swing and wherein the reference signal is obtained from the following forearm and the second signal is obtained from the lead calf portion of the leg.

17. A self-contained biofeedback device for monitoring muscle activity during a golf swing, said device including a band adapted for securement around the arm of the golfer, said band carrying a pair of spaced surface electrodes adapted to make contact with an arm muscle for receipt of electrical voltage from the muscle, said electrodes being in continuity with differential amplifier means and means for measuring amplified differential voltage, means for reporting the amplified differential voltage, and a sound emitting device communicating with said means for reporting voltage, said amplifier means, and measuring means for differential voltage, said amplifier means, measuring means, reporting means and sound emitting means being carried by said band, wherein the sound being emitted by said device changes when said muscle tenses.

18. The device of claim 17 wherein said reporting means comprises a liquid crystal display.

* * * * *